(12) United States Patent
Closson et al.

(10) Patent No.: US 8,357,810 B2
(45) Date of Patent: *Jan. 22, 2013

(54) 3.2.1-BICYCLO-OCTANE COMPOUNDS

(75) Inventors: Adam P. Closson, Red Bank, NJ (US); Benjamin Amorelli, Farmingdale, NJ (US); Nicole O'Keefe, Brick, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/901,092

(22) Filed: Oct. 8, 2010

(65) Prior Publication Data

US 2012/0088922 A1    Apr. 12, 2012

(51) Int. Cl.
C07D 317/72 (2006.01)
C07D 307/93 (2006.01)
C07D 303/64 (2006.01)
C07C 49/553 (2006.01)
A61K 8/18 (2006.01)
A61Q 90/00 (2009.01)

(52) U.S. Cl. ........ 549/336; 549/459; 549/545; 568/374; 512/9; 512/12; 512/13; 512/27

(58) Field of Classification Search ............... 549/336, 549/459, 545; 568/374; 512/9, 12, 13, 27
See application file for complete search history.

(56) References Cited

OTHER PUBLICATIONS

Kreiser et al, Liebigs Ann. Chem. p. 194-202 (1985).*

* cited by examiner

*Primary Examiner* — Bernard Dentz
(74) *Attorney, Agent, or Firm* — Elizabeth M. Quirk; XuFan Tseng; Joseph F. Leightner

(57) ABSTRACT

The present invention relates to novel compounds and their use in fragrance compositions. Novel 3.2.1-bicyclo-octane compounds of the present invention are represented by formula:

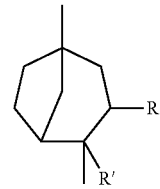

wherein R is selected from the group consisting of carbonyl and [1,3]dioxolane;
R' is selected from the group consisting of hydrogen and allyl;
or R and R' taken together represent

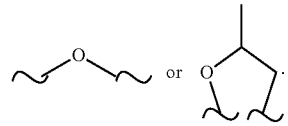

6 Claims, No Drawings

3.2.1-BICYCLO-OCTANE COMPOUNDS

FIELD OF THE INVENTION

The present invention relates to novel chemical entities, a method of using the same as fragrance materials, and a method of using the same as malodor counteracting materials.

BACKGROUND OF THE INVENTION

There is an ongoing need in the fragrance industry to provide new chemicals to give perfumers and other persons the ability to create new fragrances for perfumes, colognes and personal care products.

A particular effort in the fragrance industry has also been made to provide new chemicals to treat and control malodors. "Malodor" is a term used to describe undesirable or unpleasant odor. Common sources of malodors include body perspiration, smoke, environmental odor such as mold and mildew, bathroom, and etc. Conventional perfumes including a variety of fragrance materials are developed to mask malodors, which generally function via two mechanisms: first, the fragrance materials blend with the malodor compound to provide a different and more desirable aroma; and second, the fragrance materials are employed to overwhelm the malodor compound. However, a large quantity of fragrance materials is required for both mechanisms, which in itself is often undesirable. Thus, there remains a need for new chemicals that are effective in counteracting malodors.

SUMMARY OF THE INVENTION

The present invention provides novel 3.2.1-bicyclo-octane compounds, the unexpected advantageous use thereof in enhancing, improving or modifying the fragrance of perfumes, colognes, toilet waters, fabric care products, personal products, and the like, and the unexpected advantageous use thereof in counteracting malodors.

One embodiment of the invention relates to novel 3.2.1-bicyclo-octane compounds represented by Formula Ia set forth below:

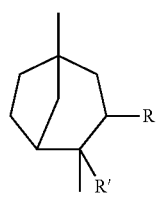

Formula Ia wherein R is selected from the group consisting of oxo and [1,3]dioxolane;
R' is selected from the group consisting of hydrogen and allyl;
or R and R' taken together represent

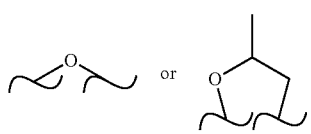

Another embodiment of the invention relates to novel 3.2.1-bicyclo-octane compounds represented by Formula Ib set forth below:

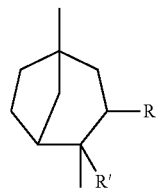

Formula Ib wherein R is selected from the group consisting of oxo and [1,3]dioxolane;
R' is selected from the group consisting of hydrogen and allyl;
or R and R' taken together represent

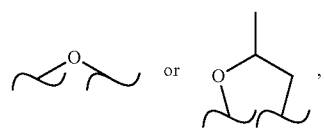

with the proviso that when R is oxo, R' is allyl.

Another embodiment of the invention relates to a method of improving, enhancing or modifying a fragrance formulation through the addition of an olfactory acceptable amount of the novel compounds represented by Formula Ia and Formula Ib provided above.

Another embodiment of the invention relates to a fragrance composition comprising the novel compounds represented by Formula Ia and Formula Ib provided above.

Another embodiment of the invention relates to a method of counteracting a malodor in air space or a substrate comprising the step of introducing a malodor counteracting effective amount of the novel compounds represented by Formula Ia and Formula Ib provided above.

Another embodiment of the invention relates to a malodor counteracting composition comprising the novel compounds represented by Formula Ia and Formula Ib provided above.

These and other embodiments of the present invention will be apparent by reading the following specification.

DETAILED DESCRIPTION OF THE INVENTION

In Formula Ia above, R is oxo or [1,3]dioxolane, R' is hydrogen or allyl, or R and R' taken together represent

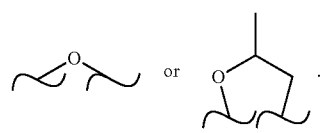

In Formula Ib above, R and R', respectively, are defined the same as R and R' in Formula Ia, with the proviso that when R is oxo, R' is allyl.

In one embodiment of the invention, the novel compounds of the present invention are represented by the following structures:

Structure 1

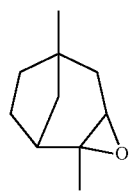

Structure 2

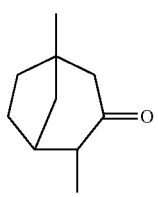

Structure 3

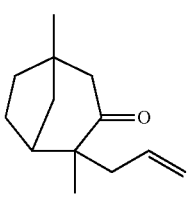

Structure 4

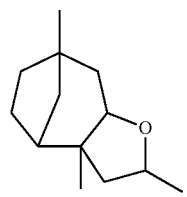

Structure 5

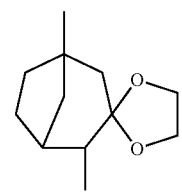

Those with the skill in the art will appreciate that

Structure 1 is 2,6-dimethyl-3-oxa-tricyclo[4.2.1.0*2,4*]nonane;

Structure 2 is 1,4-dimethyl-bicyclo[3.2.1]octan-3-one;

Structure 3 is 4-allyl-1,4-dimethyl-bicyclo[3.2.1]octan-3-one;

Structure 4 is 2,4,8-trimethyl-5-oxa-tricyclo[6.2.1.0*2,6*]undecane; and

Structure 5 is 1,4-dimethyl-bicyclo[3.2.1]octan-3-dioxolane.

Novel 3.2.1-bicyclo-octane compounds of the present invention can be prepared with 1,4-dimethyl-4-vinyl-cyclohexene (commercially available from Evonik Industries) according to a reaction scheme shown as follows:

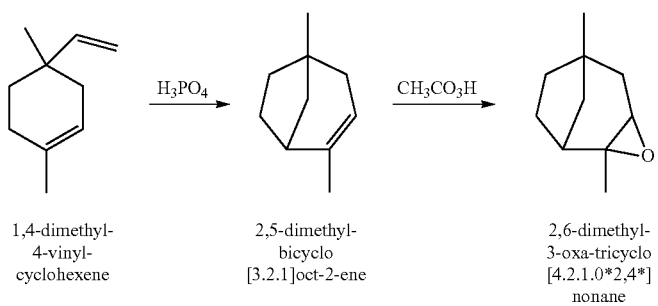

1,4-dimethyl-4-vinyl-cyclohexene → 2,5-dimethyl-bicyclo[3.2.1]oct-2-ene → 2,6-dimethyl-3-oxa-tricyclo[4.2.1.0*2,4*]nonane

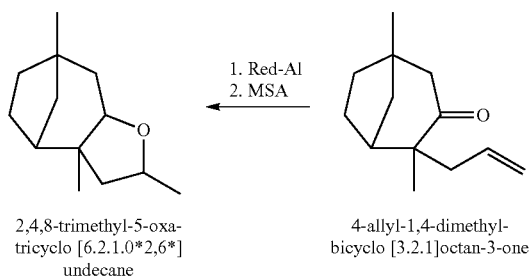

2,4,8-trimethyl-5-oxa-tricyclo[6.2.1.0*2,6*]undecane ← 4-allyl-1,4-dimethyl-bicyclo[3.2.1]octan-3-one

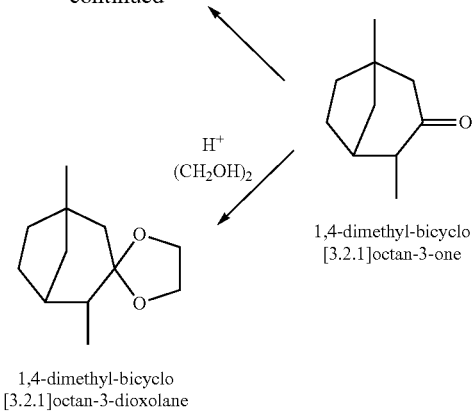

1,4-dimethyl-bicyclo
[3.2.1]octan-3-dioxolane 1,4-dimethyl-bicyclo
[3.2.1]octan-3-one Those with skill in the art will recognize that the compounds of the present invention may have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and solid phase microextraction, referred to as SPME.

The compounds of the present invention are surprisingly found to possess unexpected green, fruity, and woody notes. The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation may vary from about 0.005 to about 50 weight percent, preferably from about 0.01 to about 20 weight percent, and more preferably from about 0.05 to about 5 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention. When used in a fragrance formulation, the compounds of the present invention unexpectedly provide green, fruity, and woody characteristics and make the fragrance formulation more desirable and noticeable. The compounds of the present invention assist in beautifying and enhancing the finished accord and improve the performance of other materials in the fragrance formulation.

The compounds of the present invention are further surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. All reagents were purchased from Sigma-Aldrich, Inc. unless otherwise noted. Further, as used herein all percentages are weight percent unless otherwise noted, mol is understood to be mole, mL is understood to be milliliter, L is understood to be liter, g is understood to be gram, Kg is understood to be kilogram, and mmHg be millimeters (mm) of mercury (Hg). IFF as used in the examples is understood to mean International Flavors & Fragrances Inc., New York, N.Y., USA.

EXAMPLE I

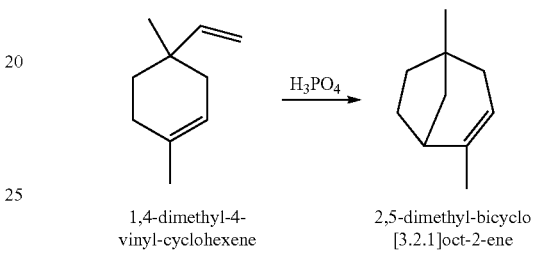

1,4-dimethyl-4-vinyl-cyclohexene → 2,5-dimethyl-bicyclo[3.2.1]oct-2-ene

Preparation of 2,5-Dimethyl-bicyclo[3.2.1]oct-2-ene: Phosphoric acid ($H_3PO_4$, 145 g, 1.48 mol) was added to a solution of 1,4-dimethyl-4-vinyl-cyclohexene (403 g, 2.96 mol, commercially available from Evonik Industries) in toluene (500 mL) and refluxed for 6 hours. The reaction mixture was subsequently quenched with a solution of sodium hydroxide (NaOH). The organic layer was separated, dried over sodium sulfate ($Na_2SO4$), and fractionated to provide 2,5-dimethyl-bicyclo[3.2.1]oct-2-ene (280 g) having a boiling point of 87° C. at a pressure of 27 mmHg $^1$H NMR: 1.09 ppm (s, 3H), 1.33-1.58 ppm (m, 4H), 1.65 ppm (s, 3H), 1.68-1.82 ppm (m, 3H), 2.08 ppm (d, 1H, J=17 Hz), 2.17 ppm (t, 1H, J=4 Hz), 5.07 ppm (m, 1H)

2,5-Dimethyl-bicyclo[3.2.1]oct-2-ene was described as having green, terpineol, woody, and black pepper notes.

EXAMPLE II

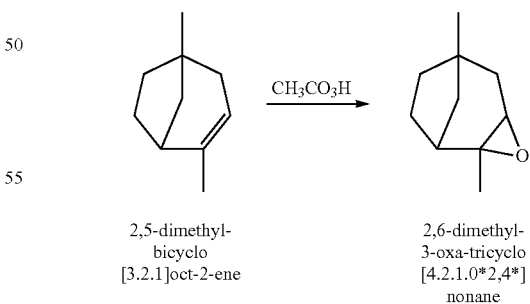

2,5-dimethyl-bicyclo[3.2.1]oct-2-ene → 2,6-dimethyl-3-oxa-tricyclo[4.2.1.0*2,4*]nonane Preparation of 2,6-Dimethyl-3-oxa-tricyclo[4.2.1.0*2,4*]nonane (Structure 1): 2,5-Dimethyl-bicyclo[3.2.1]oct-2-ene (800 g, 5.88 mol, obtained as above in EXAMPLE I) was fed into a solution of peracetic acid ($CH_3CO_3H$, 32%, 1.466 Kg, 6.18 mol) and sodium acetate ($CH_3CO_2Na$, 72 g, 0.882 mol), and cooled to 0° C. The reaction mixture was aged for 6 hours, and subsequently quenched with water and toluene. The reaction mixture was shaken and split. The organic layer was first washed with a solution of sodium carbonate (Na$_2$CO$_3$), and then with a solution of sodium sulfite (Na$_2$SO$_3$). Fractional distillation of the organic layer provided 2,6-dimethyl-3-oxa-tricyclo[4.2.1.0*2,4*]nonane (734 g) having a boiling point of 31° C. at a pressure of 18 mmHg $^1$H NMR: 0.92-1.34 ppm (m, 1H), 0.97 ppm (s, 3H), 1.31 ppm (s, 3H), 1.46 ppm (t, 2H, J=7.7 Hz), 1.61 ppm (d, 1H, J=15.0 Hz), 1.68-1.83 ppm (m, 4H), 2.21 ppm (t, 1H, J=5.0 Hz), 2.79 ppm (d, 1H, J=4.6 Hz)

2,6-Dimethyl-3-oxa-tricyclo[4.2.1.0*2,4*]nonane was described as having camphor, woody, fresh, sweet, minty, and thujone-like notes.

EXAMPLE III

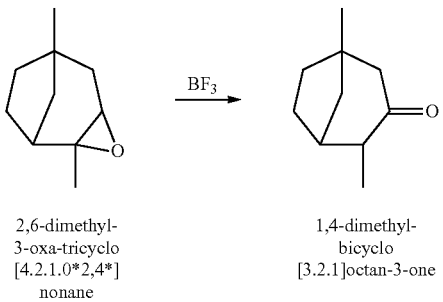

2,6-dimethyl-
3-oxa-tricyclo
[4.2.1.0*2,4*]
nonane 1,4-dimethyl-
bicyclo
[3.2.1]octan-3-one Preparation of 1,4-Dimethyl-bicyclo[3.2.1]octan-3-one (Structure 2): 2,6-Dimethyl-3-oxa-tricyclo[4.2.1.0*2,4*] nonane (381 g, 2.51 mol, obtained as above in EXAMPLE II) was fed into a solution of boron trifluoride diethyletherate (BF$_3$.O(C$_2$H$_5$)$_2$, BF$_3$, 35 g, 0.251 mol) in toluene (500 mL) while the pot temperature was maintained at about 30° C. and the aging process continued for 6 hours. The reaction mixture was subsequently quenched with water and washed with a Na$_2$CO$_3$ solution. Fractional distillation of the organic layer provided 1,4-dimethyl-bicyclo[3.2.1]octan-3-one (337 g) having a boiling point of 43° C. at a pressure of 1 mmHg $^1$H NMR: 0.99 ppm (d, ~34% of 3H, J=6.5 Hz), 1.12 ppm (d, ~66% of 3H, J=6.5 Hz), 1.13 ppm (s, 3H), 1.23-1.54 ppm (m, 4H), 1.62-2.44 ppm (m, 4H), 1.82 ppm (d, ~34% of 1H, J=11.6 Hz), 1.88 ppm (d, ~66% of 1H, J=12.2 Hz), 2.14 ppm (d, ~34% of 1H, J=15.8 Hz)

1,4-Dimethyl-bicyclo[3.2.1]octan-3-one was described as having woody, fresh, minty, and menthol notes.

EXAMPLE IV

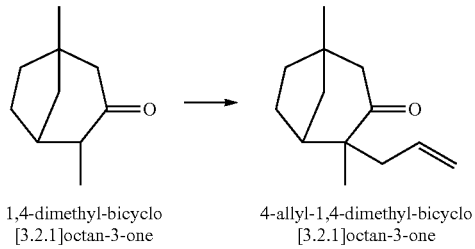

1,4-dimethyl-bicyclo
[3.2.1]octan-3-one 4-allyl-1,4-dimethyl-bicyclo
[3.2.1]octan-3-one Preparation of 4-Allyl-1,4-dimethyl-bicyclo[3.2.1]octan-3-one (Structure 3): Hydrochloric acid (HCl, 6 g) was added to a solution of 1,4-dimethyl-bicyclo[3.2.1]octan-3-one (400 g, 2.6 mol, obtained as above in EXAMPLE III), trimethylorthoformate (HC(OCH$_3$)$_3$, 280 g, 2.6 mol), and methanol (CH$_3$OH, 400 mL). The reaction mixture was aged for 3 hours and subsequently quenched with a NaOH solution. Allyl alcohol (CH$_2$CHCH$_2$OH, 300 g, 5.2 mol), acetic acid (CH$_3$COOH, 50 g), and methanesulfonic acid (CH$_3$SO$_2$OH, MSA, 5 g) were added and aged at reflux. The volatile ingredients were distilled off with a Dean Stark trap. The resulting mixture was washed with a Na$_2$CO$_3$ solution. Fractional distillation of the organic layer provided 4-allyl-1,4-dimethyl-bicyclo[3.2.1]octan-3-one (127 g) having a boiling point of 64° C. at a pressure of 0.2 mmHg $^1$H NMR: 1.02 ppm (s, 3H), 1.13 ppm (s, 3H), 1.35-1.48 ppm (m, 3H), 1.58-1.67 ppm (m, 1H), 1.69-1.78 ppm (m, 1H), 2.03-2.13 ppm (m, 3H), 2.22-2.33 ppm (m, 2H), 2.46-2.49 ppm (d, 1H, J=14.2 Hz), 5.01-5.10 ppm (m, 2H), 5.61-5.73 ppm (m, 1H)

4-Allyl-1,4-dimethyl-bicyclo[3.2.1]octan-3-one was described as having amber, fruity, dusty, and musty notes.

EXAMPLE V

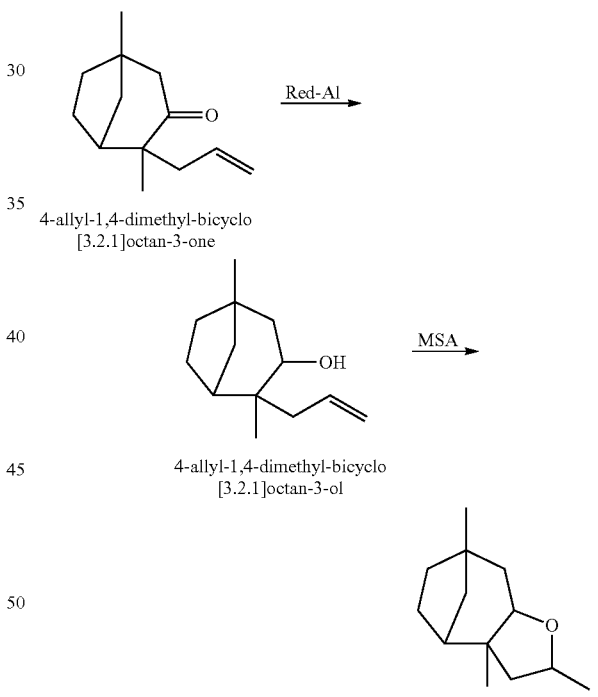

4-allyl-1,4-dimethyl-bicyclo
[3.2.1]octan-3-one 4-allyl-1,4-dimethyl-bicyclo
[3.2.1]octan-3-ol 2,4,8-trimethyl-5-oxa-tricyclo
[6.2.1.0*2,6*]undecane Preparation of 2,4,8-Trimethyl-5-oxa-tricyclo[6.2.1.0*2, 6*]undecane (Structure 4): 4-Allyl-1,4-dimethyl-bicyclo [3.2.1]octan-3-one (288 g, 1.5 mol, obtained as above in EXAMPLE IV) was added to a solution of Red-Al (65%, 506 g, 1.5 mol) in toluene at 75° C. The reaction mixture was aged for 3 hours while the temperature was maintained at 75° C., then cooled to room temperature, and subsequently quenched with a solution of sodium bicarbonate (NaHCO$_3$). Distillation of the organic layer provided 4-allyl-1,4-dimethyl-bicyclo[3.2.1]octan-3-ol (288 g, 1.5 mol), which was then added to a MSA solution (30 g) in toluene (500 mL) and heated to reflux for 3 hours. The reaction mixture was subsequently washed with a Na$_2$CO$_3$ solution. Fractional distillation of the organic layer provided 2,4,8-trimethyl-5-oxa-tricyclo[6.2.1.0*2,6*]undecane (170 g) having a boiling point of 62° C. at a pressure of 0.3 mmHg $^1$H NMR: 1.01 ppm (s, 3H), 1.11 ppm (s, 3H), 1.12-1.42 ppm (m, 4H), 1.30 ppm (d, 3H, J=6.1 Hz), 1.50 ppm (d, 1H, J=12.1 Hz, of d, J=6.0 Hz), 1.62-1.90 ppm (m, 5H), 1.98 ppm (t, 1H, J=5.5 Hz), 3.60 ppm (t, 1H, J=8.3 Hz), 4.29 ppm (m, 1H)

2,4,8-Trimethyl-5-oxa-tricyclo[6.2.1.0*2,6*]undecane was described as having green, earthy, fruity, fresh, and woody notes.

EXAMPLE VI

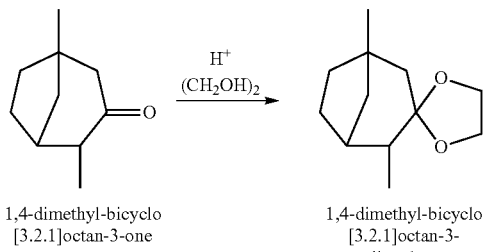

1,4-dimethyl-bicyclo[3.2.1]octan-3-one → 1,4-dimethyl-bicyclo[3.2.1]octan-3-dioxolane Preparation of 1,4-Dimethyl-bicyclo[3.2.1]octan-3-dioxolane (Structure 5): 1,4-Dimethyl-bicyclo[3.2.1]octan-3-one (205 g, 1.35 mol, obtained as above in EXAMPLE III) was added to a solution of ethylene glycol ((CH$_2$OH)$_2$, 103 g, 1.69 mol) and PTSA (10 g), and refluxed for 4 hours. The reaction mixture was subsequently washed with water followed by a Na$_2$CO$_3$ solution. Fractional distillation of the organic layer provided the 1,4-dimethyl-bicyclo[3.2.1]octan-3-dioxolane (217 g) having a boiling point of 60° C. at a pressure of 16 mmHg.

$^1$H NMR: 0.83-0.97 ppm (3d, 3H), 0.99-1.03 ppm (2s, 3H), 1.07-1.54 ppm (m, 6H), 1.61-2.12 ppm (m, 4H), 3.72-3.99 ppm (m, 4H)

1,4-Dimethyl-bicyclo[3.2.1]octan-3-dioxolane was described as having fruity, fresh, and camphor notes.

EXAMPLE VII

The fragrance formulas exemplified as follows demonstrated that 2,4,8-trimethyl-5-oxa-tricyclo[6.2.1.0*2,6*]undecane (Structure 4) imparted green, earthy, fruity, fresh, and woody notes to a fragrance formula.

| Ingredients | Parts* + | Parts* − |
|---|---|---|
| Acalea | 5.00 | 5.00 |
| Acetaldehyde Dimethylacetal | 0.12 | 0.12 |
| Decanal | 0.44 | 0.44 |
| Allyl Amyl Glycolate 0.1% DPG | 0.88 | 0.88 |
| Allyl Cyclohexane Propionate | 2.00 | 2.00 |
| Allyl Heptanoate | 2.00 | 2.00 |
| Applelide ® | 5.00 | 5.00 |
| Benzyl Acetate | 0.44 | 0.44 |
| Bornafix ® | 0.44 | 0.44 |
| Cashmeran | 0.20 | 0.20 |
| Coumarin | 0.18 | 0.18 |
| CP Formate Aphermate | 9.94 | 9.94 |
| Cyclobutanate ® | 0.18 | 0.18 |
| Damascone, Alpha | 0.50 | 0.50 |
| Dihydro Myrcenol | 5.00 | 5.00 |
| Dipropylene Glycol | — | 1.00 |
| 2,4,8-Trimethyl-5-oxa-tricyclo[6.2.1.0*2,6*]undecane | 1.00 | — |
| Ethyl Vanillin | 0.09 | 0.09 |
| Ethyl-2-methyl butyrate | 3.50 | 3.50 |
| Fleuranil 10% DPG ® | 0.88 | 0.88 |
| Floriffol ® | 8.06 | 8.06 |
| Galaxolide | 9.80 | 9.80 |
| Galbascone | 0.10 | 0.10 |
| Grisalva | 0.30 | 0.30 |
| Hexyl Butyrate | 0.88 | 0.88 |
| Ionol | 0.09 | 0.09 |
| Ionone, Alpha | 1.00 | 1.00 |
| Iso Amyl Butyrate | 0.20 | 0.20 |
| Iso E Super | 4.38 | 4.38 |
| Lemorosa | 4.38 | 4.38 |
| Lilial | 1.61 | 1.61 |
| Lyral | 1.61 | 1.61 |
| Mandarin Oil | 1.75 | 1.75 |
| Mango Ester 10% DPG | 0.01 | 0.01 |
| Methyl Anthranilate ® | 0.44 | 0.44 |
| Methyl Dihydro Jasmonate | 5.00 | 5.00 |
| Mimosa Absolute | 0.20 | 0.20 |
| Musk Z4 | 1.00 | 1.00 |
| Nebulone ® | 6.00 | 6.00 |
| Orange Oil | 1.75 | 1.75 |
| Ozofleur ® | 1.07 | 1.07 |
| Prenyl Acetate | 2.63 | 2.63 |
| Trisamber ® | 0.44 | 0.44 |
| Undecalactone, Gamma | 0.88 | 0.88 |
| Undecavertol | 1.31 | 1.31 |
| Verdox | 5.32 | 5.32 |
| Vertoliff | 2.00 | 2.00 |
| Total | 100 | 100 |

*"+" represents a 2,4,8-trimethyl-5-oxa-tricyclo[6.2.1.0*2,6*]undecane containing formula; and "−" represents a 2,4,8-trimethyl-5-oxa-tricyclo[6.2.1.0*2,6*]undecane non-containing formula.

What is claimed is:
1. A compound of formula:

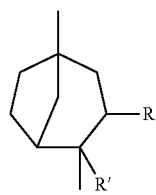

wherein R is selected from the group consisting of oxo and [1,3]dioxolane;

R' is selected from the group consisting of hydrogen and allyl;

or R and R' taken together represent

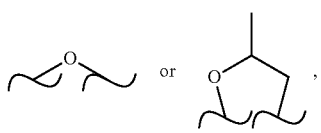

with the proviso that when R is oxo, R' is allyl.

2. The compound of claim 1, wherein the compound is selected from the group consisting of
2,6-dimethyl-3-oxa-tricyclo[4.2.1.0*2,4*]nonane;
4-allyl-1,4-dimethyl-bicyclo[3.2.1]octan-3-one;
2,4,8-trimethyl-5-oxa-tricyclo[6.2.1.0*2,6*]undecane; and
1,4-dimethyl-bicyclo[3.2.1]octan-3-dioxolane.

3. A fragrance composition comprising a compound of formula:

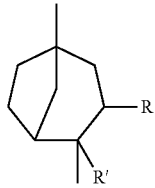

wherein R is selected from the group consisting of oxo and [1,3]dioxolane;
R' is selected from the group consisting of hydrogen and allyl;
or R and R' taken together represent

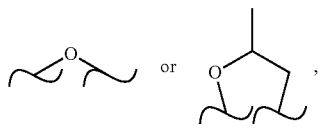

with the proviso that when R is carbonyl oxo, R' is allyl.

4. The fragrance composition of claim 3, wherein the compound is selected from the group consisting of
2,6-dimethyl-3-oxa-tricyclo[4.2.1.0*2,4*]nonane;
4-allyl-1,4-dimethyl-bicyclo[3.2.1]octan-3-one;
2,4,8-trimethyl-5-oxa-tricyclo[6.2.1.0*2,6*]undecane; and
1,4-dimethyl-bicyclo[3.2.1]octan-3-dioxolane; and
a mixture thereof.

5. A fragrance product comprising a compound of formula:

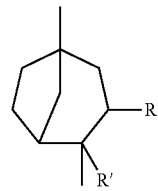

wherein R is selected from the group consisting of oxo and [1,3]dioxolane;
R' is selected from the group consisting of hydrogen and allyl;
or R and R' taken together represent

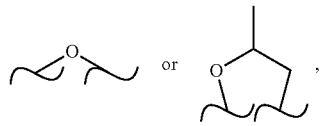

with the proviso that when R is oxo, R' is allyl.

6. The fragrance product of claim 5, wherein the compound is selected from the group consisting of
2,6-dimethyl-3-oxa-tricyclo[4.2.1.0*2,4*]nonane;
4-allyl-1,4-dimethyl-bicyclo[3.2.1]octan-3-one;
2,4,8-trimethyl-5-oxa-tricyclo[6.2.1.0*2,6*]undecane; and
1,4-dimethyl-bicyclo[3.2.1]octan-3-dioxolane; and
a mixture thereof.

* * * * *